(12) United States Patent
Rodriguez

(10) Patent No.: US 7,949,410 B2
(45) Date of Patent: May 24, 2011

(54) BURR HOLE CAP AND METHODS OF USE

(75) Inventor: Daniel Rodriguez, Sachse, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 994 days.

(21) Appl. No.: 11/696,425

(22) Filed: Apr. 4, 2007

(65) Prior Publication Data

US 2007/0233158 A1 Oct. 4, 2007

Related U.S. Application Data

(60) Provisional application No. 60/744,228, filed on Apr. 4, 2006.

(51) Int. Cl.
*A61N 1/00* (2006.01)
(52) U.S. Cl. ...................................................... 607/116
(58) Field of Classification Search .......... 206/722–728; 600/378, 383; 607/116; 606/130
See application file for complete search history.

(56) References Cited

U.S. PATENT DOCUMENTS

| 5,954,687 | A | 9/1999 | Baudino |
| 6,134,477 | A | 10/2000 | Knuteson |
| 7,454,251 | B2 | 11/2008 | Rezai et al. |
| 7,580,756 | B2 | 8/2009 | Schulte et al. |
| 2002/0052610 | A1 | 5/2002 | Skakoon et al. |
| 2005/0192594 | A1 | 9/2005 | Skakoon et al. |
| 2009/0088826 | A1 | 4/2009 | Bedenbaugh |

*Primary Examiner* — Eric D. Bertram
*Assistant Examiner* — Elizabeth K So
(74) *Attorney, Agent, or Firm* — Christopher S. L. Crawford; Craig Hoersten; Melissa Acosta

(57) ABSTRACT

In one embodiment, an apparatus for securing a lead within a burr hole comprises: an annular body structure adapted to be at least partially inserted within the burr hole; a lead retainer structure mechanically coupled to the annular body structure and adapted to be rotated along an inner perimeter of the annular body structure; the lead retainer structure including a lead engaging member for capturing the lead, wherein the lead engaging member pivots relative to the lead retainer structure; and a fixation member that is adapted to lock the lead retainer structure in place after the lead has been captured by the lead engaging member.

5 Claims, 3 Drawing Sheets

BURR HOLE CAP AND METHODS OF USE

RELATED APPLICATION

The present application claims the benefit of U.S. Provisional Patent Application Ser. No. 60/744,228, entitled "BURR HOLE CAP AND METHODS OF USE," filed Apr. 4, 2006, which is incorporated herein by reference.

TECHNICAL FIELD

The present application is generally related to burr hole cap devices which are used to hold a lead, catheter, or cannula within a burr hole in a patient's skull.

BACKGROUND

Deep brain stimulation (DBS) refers to the delivery of electrical pulses into one or several specific sites within the brain of a patient to treat various disorders. For example, DBS has been proposed as a clinical technique for treatment of chronic pain, essential tremor, Parkinson's disease (PD), dystonia, epilepsy, depression, obsessive-compulsive disorder, and other disorders.

A DBS procedure typically involves first obtaining preoperative images of the patient's brain (e.g., using computer tomography (CT) or magnetic resonance imaging (MRI)). The imaging process sometimes involves first affixing to the patient's skull fiducial markers that are discernable on the images produced by the imaging process. The fiducial markers assist in registering the preoperative images to the actual physical position of the patient in the operating room during the subsequent surgical procedure. Using the preoperative images, the neurosurgeon can select a target region within the brain, an entry point on the patient's skull, and a desired trajectory between the entry point and the target region. The entry point and trajectory are carefully selected to avoid intersecting or otherwise damaging critical brain structures.

In the operating room, the patient is immobilized and the patient's actual physical position is registered. The physician marks the entry point on the patient's skull and drills a burr hole at that location. A mechanism is provided to precisely control the path through the patient's brain to the desired location. Specifically, a positioning error on the order of a millimeter can have a significant negative effect on the efficacy of the DBS therapy. Stereotactic instrumentation and trajectory guide devices are commercially available products that facilitate the control of the trajectory and positioning of a lead during the surgical procedure.

A microdrive introducer can be used to insert a deep brain stimulation lead toward the selected region of the brain along the selected trajectory. The lead provides one or several conductive paths to deliver stimulation pulses to the selected region. The lead includes a very small diameter insulative lead body with one or several conductors (e.g., stranded wires) embedded in the insulative material. The lead also includes one or several electrodes at a distal end of the lead that are electrically coupled to respective conductors. The electrodes can be used to record signals within the brain and/or to deliver electrical stimulation pulses to brain tissue. Often, the electrical activity adjacent to one or several electrodes is analyzed to determine whether the recorded signals are consistent with the targeted region of the brain. If the recorded signals are not consistent with the targeted region, an adjustment to the lead's position can be made as appropriate.

A burr hole plug or cap structure is typically utilized to retain the lead in the desired position. A burr hole structure generally includes (i) a ring or grommet-like element that is inserted into the hole first so as to protect the edges of the burr hole and (ii) a cap or plug device that is inserted into the ring or grommet-like element to secure the lead and plug the hole.

By way of example, in U.S. Pat. No. 6,044,304, a burr ring is disclosed that is secured to the skull. The burr hole plug of the '304 patent also has an upper flange portion and circumferential ribs used to position the plug in the cranium. Also, the burr hole plug described in the '304 patent includes an aperture capable of accepting a lead through a septum.

In U.S. Pat. No. 5,954,687, a device is disclosed for securing a catheter within a burr hole. The device has a series of spaced septum elements that can be selectively penetrated for fluid communication with a reservoir in the apparatus. The main objective of the device is to allow fluid access to the patient's brain through a burr hole. Anchoring of the device is not taught and there are a limited predetermined number of septum holes that can be accessed.

U.S. Pat. No. 5,927,277 describes a burr hole ring for retaining a probe relative to the skull. The burr hole ring has an engaging member with holes to receive a probe. The '277 patent also describes a method for securing a device at a desired orientation within the burr hole. Since a fixed spacing between holes is described, the device can be placed in a limited number of locations through the burr hole.

U.S. Pat. No. 5,865,842 discloses a system and method for anchoring a lead in a burr hole. The disclosed system consists of a base-plate, adaptor, seal, and screw cap. The lead is anchored mechanically at the burr hole at a 90 degree angle relative to the burr hole.

U.S. Pat. No. 5,843,150 discloses an annular clamping means with a compressible feed-through member for receiving a lead. The described order for anchoring the lead includes making the burr hole, inserting the plug ring, inserting the lead, and engaging the clamping member.

Other burr hole plug assemblies and features of burr hole plugs are taught in U.S. Pat. No. 5,464,446 (burr hole plug with a central lumen and a cap that engages with the flange of the plug); U.S. Pat. No. 4,998,938 (a device that facilitates insertion of an instrument into a patient's cranial cavity); U.S. Pat. No. 4,328,813 (a burr hole plug with a cap that anchors the lead); and U.S. Pat. No. 4,245,645 (a probe and system that is used to perform stereoelectroencephalographic exploration).

SUMMARY

In one embodiment, an apparatus for securing a lead within a burr hole comprises: an annular body structure adapted to be at least partially inserted within the burr hole; a lead retainer structure mechanically coupled to the annular body structure and adapted to be rotated along an inner perimeter of the annular body structure; the lead retainer structure including a lead engaging member for capturing the lead, wherein the lead engaging member pivots relative to the lead retainer structure; and a fixation member that is adapted to lock the lead retainer structure in place after the lead has been captured by the lead engaging member.

The foregoing has outlined rather broadly certain features and/or technical advantages in order that the detailed description that follows may be better understood. Additional features and/or advantages will be described hereinafter. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
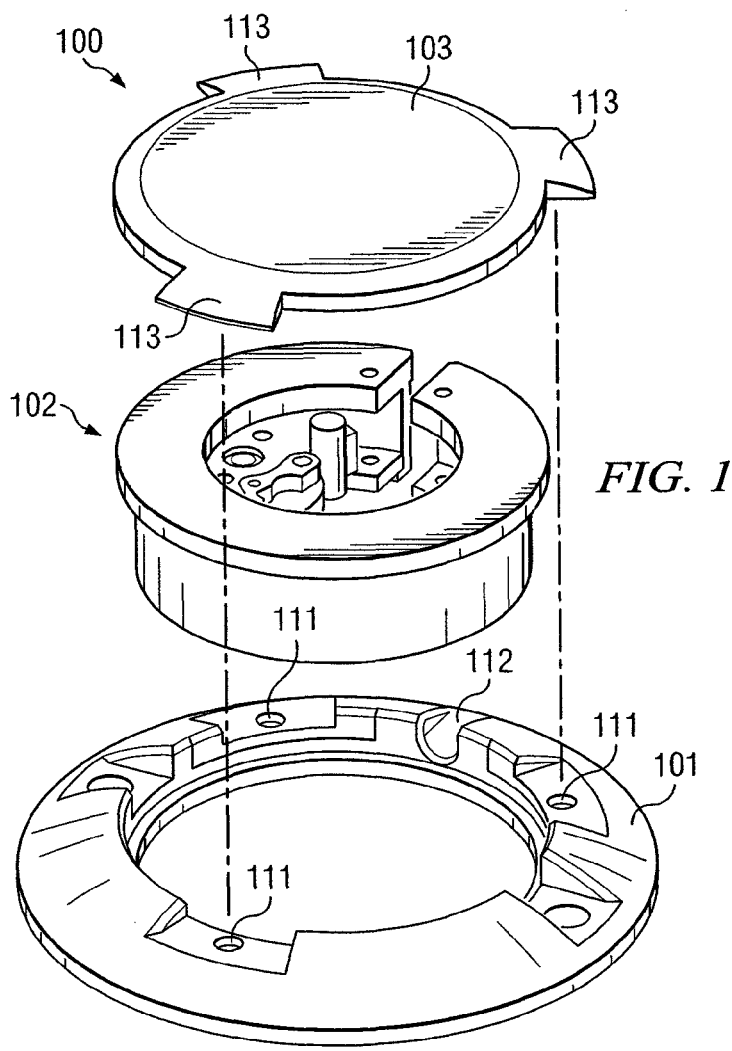
FIG. 1 depicts a disassembled view of a burr hole cap according to one representative embodiment.
Figure 4:
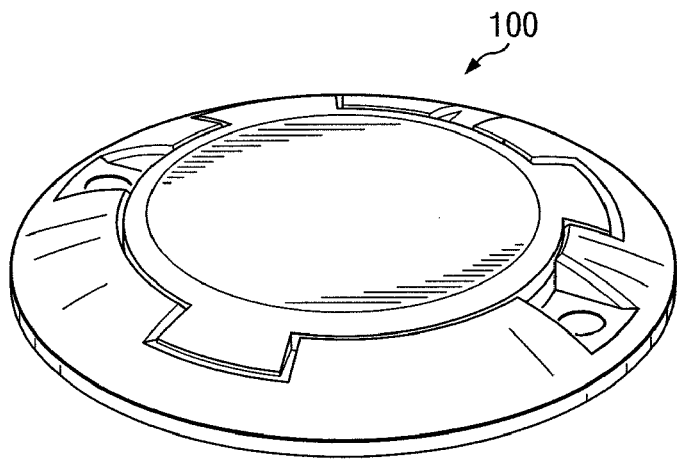
FIG. 4 depicts an assembled view of a burr hole cap according to one representative embodiment.

Referring now to the drawings, FIG. 1 depicts burr hole cap 100 in a partially disassembled form according to one representative embodiment. Burr hole cap 100 preferably comprises multiple components that are assembled at the time of lead implantation. For the purpose of this application, when the term "lead" is employed, it is intended to be interpreted broadly to include stimulation leads, infusion catheters, cannulas, and similar medical devices that can be retained within a burr hole cap device. As shown in FIG. 1, burr hole cap 100 includes cap base 101, insert assembly 102, and snap on cap 103. Insert assembly 102 fits within the central opening of cap base 101. Snap on cap 103 covers insert assembly 102 and is retained on cap base 101 via coupling of projections 113 to elements 111 of cap base 101. An assembled version of these components is shown in the illustration of burr hole cap 100 in FIG. 4.

In use, cap base 101 is secured to a patient's skull. Specifically, surgical screws (not shown) are inserted through cap base 101 into the patient's skull. Cap base 101 could alternatively be affixed to the patient's skull using an exterior threaded structure that fits into threads formed in the burr hole of the patient as an example. Cap base 101 further includes opening 112 through which the lead exits from the burr hole cap 100 to be coupled to a pulse generator.

Figure 2:
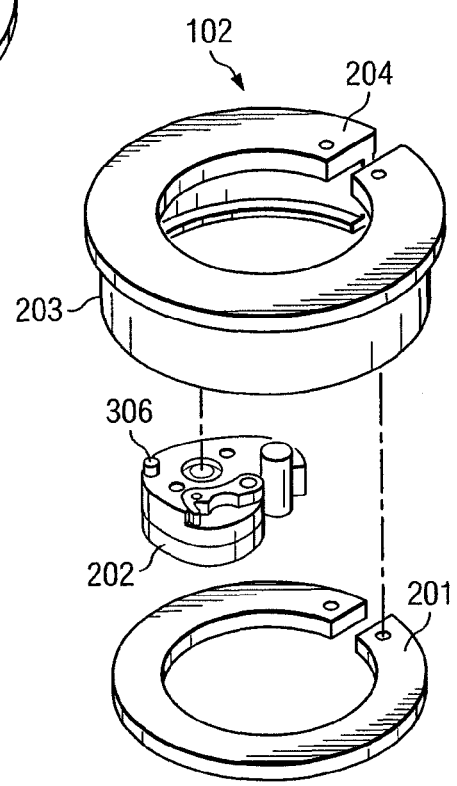
FIG. 2 depicts a disassembled view of an insertion assembly for use within a burr hole cap according to one representative embodiment.

Insert assembly 201 is shown in a disassembled form in FIG. 2 according to one representative embodiment. Insert assembly 201 is adapted to be partially located within the burr hole of the patient and to be mechanically coupled with cap base 101. Insert assembly 201 includes the components that enable a lead to be secured at a desired location anywhere within the burr hole. As shown in FIG. 2, insert assembly 201 comprises retainer 201, lead retainer 202, and housing structure 203. In preferred embodiments, housing structure 203 and lead retainer 201 are shipped in a permanently coupled configuration with a distal portion of lead retainer 202 placed between the two components, although the components could be connected at the time of surgery in alternative embodiments.

Figure 3:
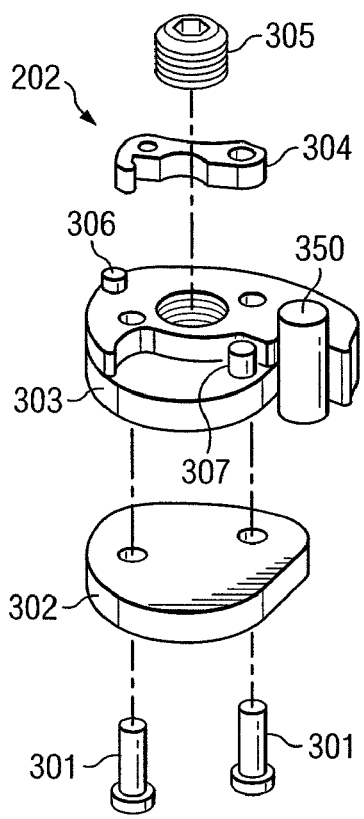
FIG. 3 depicts a disassembled view of a lead retainer for use within a burr hole cap according to one representative embodiment.

When mated, housing structure 203 and lead retainer 201 define an annular channel in which a distal portion of lead retainer 202 sits. Preferably, flange 204 of housing structure 203 comprises a lip (shown in FIG. 5A) on its underside and interior circumference. A suitable structure (e.g., a pivot pin 306 as shown in FIG. 3) is preferably implemented on lead retainer 202 that extends into the space behind the lip. Accordingly, the lip ensures that pin 306 and, hence, the distal end of lead retainer 202 is retained within the annular channel defined by housing structure 203 and lead retainer 201.

Figure 5A:
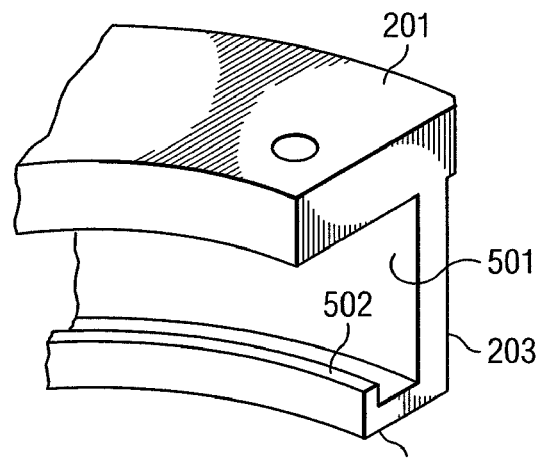
FIG. 5A depicts a cut-away view of an annular channel for defining a rotational path for a lead retainer according to one representative embodiment.
Figure 5B:
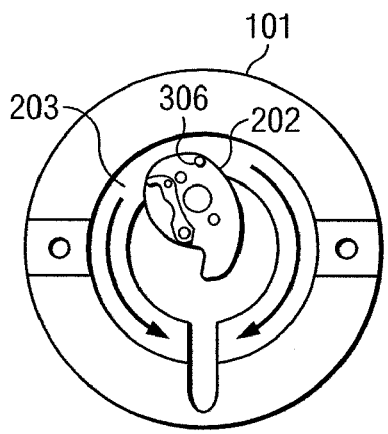
FIG. 5B depicts a top view of an insertion assembly and the rotational path along the insertion assembly that may be traversed by the lead retainer according to one representative embodiment.
Figure 5C:
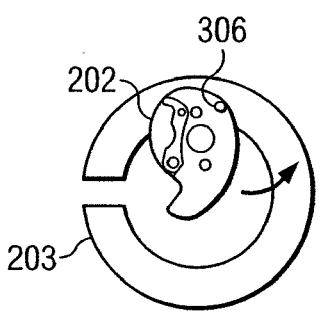
FIGS. 5C and 5D depict respective lead retainer orientations and pivotal degrees of freedom according to one representative embodiment.
Figure 5D:
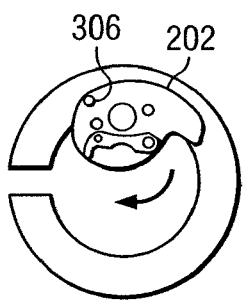

FIG. 5A depicts a cut-away view of housing structure 203 and retainer 201 showing annular channel 501 according to one representative embodiment. Lip 502 is also shown on the underside of flange 204. FIG. 5B depicts a top view of housing structure 203 and the path through which lead retainer 202 may be traversed according to one representative embodiment. As shown in FIG. 5B, the annular channel enables lead retainer 202 to rotate along the circumferential path defined by housing structure 203. FIG. 5C shows lead retainer 202 fully pivoted in the clockwise position and having pivotal freedom in the counter-clockwise direction. FIG. 5D shows lead retainer 202 fully pivoted in the counter-clockwise position and having pivotal freedom in the clockwise direction. Additionally, lead retainer 202 has some radial degree of freedom (not shown) that results from movement of the pin 306 within the radial width defined of annular channel 501. By allowing lead retainer 202 to be rotated and pivoted within the burr hole, the lead can be captured irrespective of the lead's position within the burr hole.

FIG. 3 depicts a disassembled view of lead retainer 202 according to one representative embodiment. Lead retainer 202 comprises lead holder base structure 303 which includes pivot pin 306 and clamp pin 307. One end of clamp 307 fits over clamp pin 307 and rotates about pin 307. After lead holder base 307 is rotated and/or pivoted as shown in FIGS. 5B-5D such that the lead 350 is positioned within the recess of lead holder base structure 303, clamp 307 is rotated about pin 307 to capture lead 350. Set screw 305 is rotated to cause pressure foot 302 (which is attached to lead holder base 307 through pins 301) to expand (the combined width of lead holder base structure 303 and pressure foot 302 is increased). The expansion of pressure foot 302 locks the lead retainer 202 in place and consequently causes lead 350 to be held at the desired position. That is, the expansion of the pressure foot 302 causes lead retainer 202 to contact the upper and lower surfaces of channel 501 (shown in FIG. 5A) with some amount of force. The contact requires a significant frictional force to be exerted on lead retainer 202 to move lead retainer 202 thereby locking lead retainer 202 in place. Although a fixation member is shown integrated with lead retainer 202, one or several fixation members could be employed elsewhere. For example, housing 204 could be implemented to selectively fix lead retainer 202 at a given position and orientation.

Figure 6:
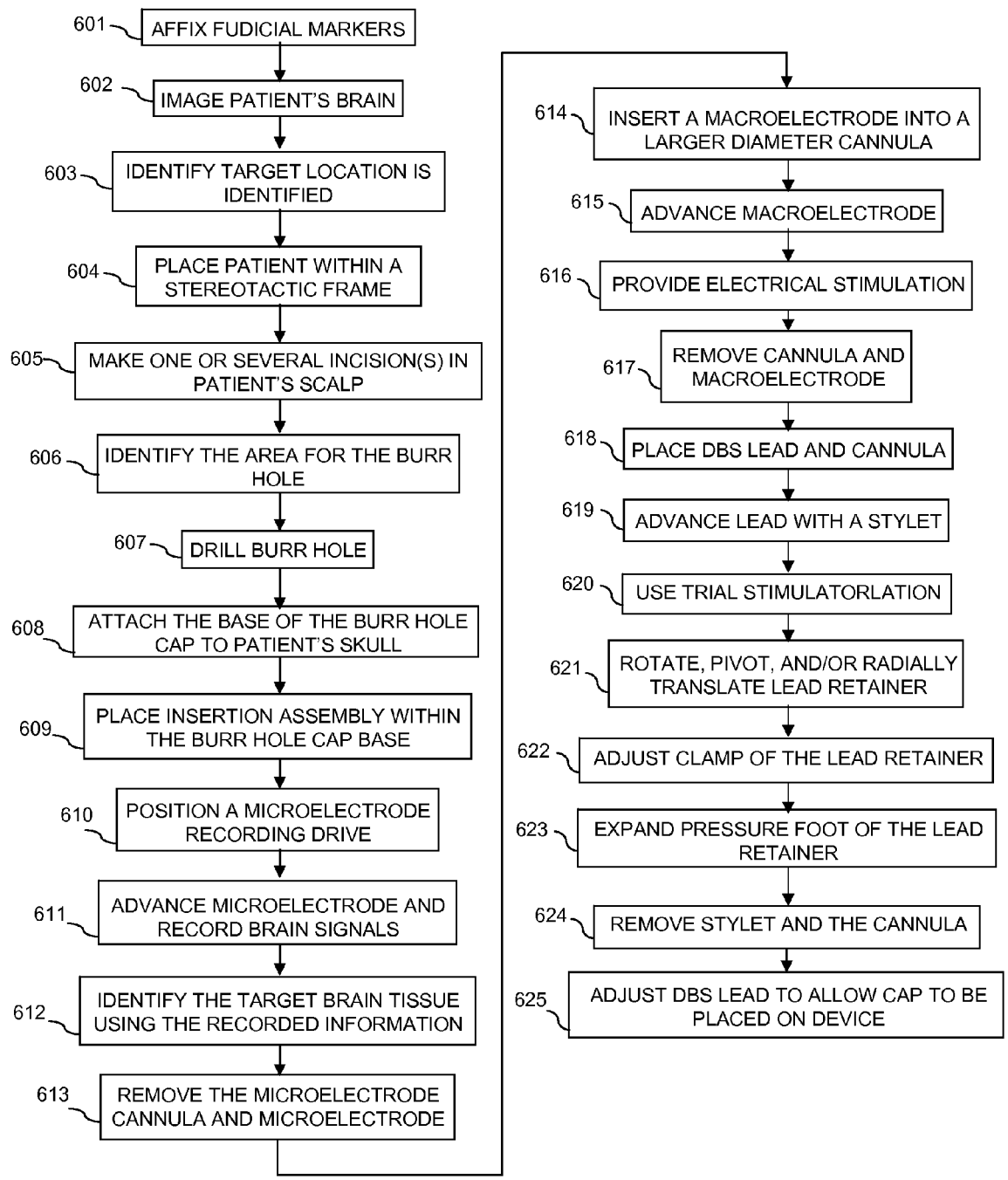
FIG. 6 depicts a flowchart for placing a lead within the skull of a patient in conjunction with use of the present burr hole cap according to one representative embodiment.

FIG. 6 depicts a flowchart for placing a lead within the skull of a patient in conjunction with use of the present burr hole cap according to one representative embodiment.

In step 601, fudicial markers are affixed to the patient's skull. In step 602, imaging of the patient's brain occurs. Any suitable imaging technology can be utilized such as MRI systems, CT systems, etc. The imaging may also involve functional analysis of the brain in response to specific stimuli. For example, a functional MRI process may be performed in which stimuli is provided to the patient and the MRI imaging is utilized to identify the specific structures in the brain that respond to the stimuli. In step 603, based upon the imaging information, a target location is identified. Commercially available navigational software can be used to relate the fudicial markers to desired target location. Specifically, the navigational software uses the identified target location with the imaging information of the patient's brain and the fiducial markers to calculate a location for the burr hole and a path for traversal of the DBS lead to the target location. The location of the burr hole and the path are selected to avoid damaging relevant structures of the brain.

In step 604, the patient is placed within a stereotactic frame in a head rest. In step 605, one or several incision(s) may be made on the patient's scalp. In step 606, an identification of the area for the burr hole is made on the patient's skull within the area exposed by the incision(s). In step 607, the burr hole is drilled. In step 608, the base of the burr hole cap is attached to the patient's skull using surgical screws. In step 609, the insertion assembly is placed within the burr hole cap base and into the burr hole.

In step 610, a microelectrode recording drive is positioned using a stereotatic arc (in relation to the fudicial markers) and the stored navigational data and a microelectrode cannula is placed within the drive. In step 611, the microelectrode is advanced along the predetermined tract and the brain signals detected by the microelectrode are recorded. In step 612, the target brain tissue is identified using the recorded information. In step 613, the microelectrode cannula and microelectrode are removed.

In step 614, a macroelectrode is inserted into a larger diameter cannula. In step 615, the macroelectrode is advanced to the identified location using a microdrive. In step 616, electrical stimulation is provided to the identified location using the macroelectrode to verify that the expected result occurs from the stimulation, such as reduced tinnitus effects, reduced tremor, improved mood, etc. Variation in stimulation parameters (pulse amplitude, pulse frequency, pulse width, etc.) May occur at this stage for the purpose of obtaining optimal results from the stimulation. Also, some variation in positioning of the macroelectrode can occur for the purpose of obtaining optimal results. In step 617, the cannula and macroelectrode are removed.

In step 618, a DBS lead and cannula are placed. In step 619, the lead is advanced with a stylet to the target stimulation site. In step 620, a trial stimulator is used to perform the desired stimulation to verify the expected result of the stimulation. Some variation in positioning may occur for the purpose of obtaining optimal results. In step 621, the lead retainer is rotated, pivoted, and/or radially translated to place the recess structure of the lead retainer against the DBS lead. In step 622, the clamp of the lead retainer is adjusted to capture the DBS lead. In step 623, the pressure foot of the lead retainer is expanded to lock the lead retainer with the DBS lead in place. In step 624, the stylet and the cannula are removed. In step 625, the DBS lead is adjusted to allow the cap to be placed on the burr hole base structure.

Although DBS leads are discussed according to one representative embodiment, some representative embodiments can be utilized to secure any suitable type of lead, catheter, or probe. For example, a paddle-style cortical lead that is placed extradurally within a patient's skull could be secured according to one alternative embodiment. Alternatively, a catheter for drug infusion could be secured according to another representative embodiment.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

The invention claimed is:

1. An apparatus for securing a lead within a burr hole, comprising:
    an annular body structure adapted to be at least partially inserted within the burr hole, wherein the annular body comprises an interior path that extends over at least a substantial portion of an inner circumference of the annular body structure; and
    a lead retainer structure for immobilizing the lead within the burr hole;
        wherein the lead retainer structure comprises a first pin that is held within the interior path of annular body to permit rotation of the lead retainer structure about the substantial portion of the inner circumference of the annular body;
        wherein the lead retainer structure is further capable of pivoting about the first pin; and
        wherein the lead retainer structure comprises a second pin and a clamp that is pivotable about the second pin to capture the lead between an edge of the clamp and an edge of the lead retainer structure.

2. The apparatus of claim 1 wherein the annular body structure comprises a lip structure extending along the inner circumference of the annular body structure, and the first pin is retained within the interior path by the lip structure.

3. The apparatus of claim 1 further comprising:
    an expandable structure that frictionally locks the lead retainer structure against the annular body structure.

4. The apparatus of claim 1 further comprising:
    a cap base for attachment to a skull of the patient and for receiving the annular body structure.

5. The apparatus of claim 4 further comprising:
    a cap for coupling with the cap base after the annular body structure is inserted within the cap base.

* * * * *